(12) United States Patent
Stroup et al.

(10) Patent No.: US 9,592,365 B2
(45) Date of Patent: Mar. 14, 2017

(54) APPARATUS TO SECURE AND ADJUST FLEXIBLE CONDUIT

(71) Applicant: Sotera Wireless, Inc., San Diego, CA (US)

(72) Inventors: David Karl Stroup, El Cajon, CA (US); Jose Felix Jacquez, Jr., Spring Valley, CA (US); Arthur Deptala, Spring Valley, CA (US)

(73) Assignee: SOTERA WIRELESS, INC., San Diego, CA (US)

(*) Notice: Subject to any disclaimer, the term of this patent is extended or adjusted under 35 U.S.C. 154(b) by 0 days.

(21) Appl. No.: 13/946,465

(22) Filed: Jul. 19, 2013

(65) Prior Publication Data
US 2014/0025010 A1 Jan. 23, 2014

Related U.S. Application Data

(60) Provisional application No. 61/673,543, filed on Jul. 19, 2012.

(51) Int. Cl.
*A61M 5/32* (2006.01)
*A61M 25/02* (2006.01)

(52) U.S. Cl.
CPC ....... *A61M 25/02* (2013.01); *A61M 2025/028* (2013.01); *A61M 2025/0246* (2013.01); *A61M 2025/0266* (2013.01)

(58) Field of Classification Search
CPC .......... A61M 25/02; A61M 2025/0246; A61M 2025/0266; A61M 2025/028; A61M 2025/0206; A61M 2025/0213; A61M 2025/024; A61M 2025/026
USPC ....................................................... 604/179
See application file for complete search history.

(56) References Cited

U.S. PATENT DOCUMENTS

| | | | | |
|---|---|---|---|---|
| 4,662,873 | A | * | 5/1987 | Lash et al. ............... 604/179 |
| 5,795,335 | A | * | 8/1998 | Zinreich .................. 604/174 |
| 2002/0165493 | A1 | | 11/2002 | Bierman |
| 2011/0040257 | A1 | * | 2/2011 | Behymer et al. ......... 604/175 |
| 2012/0197206 | A1 | * | 8/2012 | Glenn ...................... 604/180 |

FOREIGN PATENT DOCUMENTS

WO 2014015254 A1 1/2014

OTHER PUBLICATIONS

International Search Report and Written Opinion issued in PCT/US2013/051270 dated Dec. 5, 2013.

* cited by examiner

*Primary Examiner* — Jason Flick
(74) *Attorney, Agent, or Firm* — Acuity Law Group, PC; Michael A. Whittaker

(57) ABSTRACT

The invention provides an apparatus and method of securing a length of flexible conduit to a subject, and adjusting the flexible conduit to a length tailored to the subject, in order to reduce or eliminate excess conduit traversing the subject's body. The apparatus comprises a base with elongate channels for accepting flexible conduit, a lid which mates with the base, and a securing member for attaching the mated base and lid to the body of the subject.

20 Claims, 6 Drawing Sheets

APPARATUS TO SECURE AND ADJUST FLEXIBLE CONDUIT

The present application claims priority to U.S. Provisional Patent Application 61/673,543, filed Jul. 19, 2012, which is hereby incorporated by reference in its entirety including all tables, figures, and claims.

BACKGROUND OF THE INVENTION

The following discussion of the background of the invention is merely provided to aid the reader in understanding the invention and is not admitted to describe or constitute prior art to the present invention.

Modern medical practice dictates that a subject undergoing medical treatment often have a variety of medical devices attached to their bodies during the course of treatment. These devices can range from intravenous lines to catheters and physiologic probes attached to insulated cable carrying one or more conductors, among other things. Many of these devices require the use of a length of flexible conduit that traverses the subject's body and connects to fluid supplies, monitoring stations, and the like. Various methods exist for affixing flexible conduit to a subject's body. However, because of differences in both s subject's size and the location on a subject's body to which medical devices are attached, an excess of flexible conduit often remains. At best, this excess of flexible conduit can be inconvenient to the patient by limiting comfort and mobility. At worst, an excess of conduit can lead to inadvertent removal of the medical device by entanglement or snagging of the excess conduit, which in turn can lead to unnecessary hospital alarms and the need to reinsert catheters or intravenous lines.

The present invention provides an apparatus and method of securing a length of flexible conduit to a subject, and adjusting that flexible conduit to a length tailored to the individual subject, in order to reduce or eliminate excess conduit traversing the subject's body.

SUMMARY OF THE INVENTION

It is the object of the present invention to provide and apparatus and method for securely and releasably attaching a length of flexible conduit to a subject, and adjusting the length of said flexible conduit. The apparatus as described herein is particularly well suited to attaching and adjusting a length of conduit on the arm of a patient undergoing medical treatment, in order to eliminate excess conduit that may interfere with patient activities.

In a first aspect, the apparatus is constructed of a base, a lid, and a securing member. The base and lid together form three approximately parallel channels into which flexible conduit can be placed. For convenience of the description, each channel is referred to as having a proximal opening at one end of the device, and a distal opening at the other end of device. By placing flexible conduit into the first channel in a proximal-to-distal orientation, into the second channel in a distal-to-proximal orientation, and into the third channel in a inserting proximal-to-distal orientation, the flexible conduit follows and "s" pattern, the length of which can be adjusted by pulling on the "s" portion of the loop of flexible conduit created as it exits one channel and turns to enter the adjacent channel.

The term "conduit" as used herein refers to a physical object in the form of an elongate tube. Conduits include, but are not limited to, cables, wires, catheters, infusion tubing, etc.

The terms "lid" and "base" are used herein for convenience to refer to two members of the apparatus which mate together to form the channels and hold the flexible conduit. These terms are not meant to refer to the relative orientation of these two members in terms of one another. By way of example, FIG. 1 depicts the lid attached to the securing member, and the base comprising the channels on a member which is not affixed to the securing member, but instead closes over the lid. This could be reversed such that the base is attached to the securing member, and the lid closes over the base.

The device components may be made from materials such as plastics which are capable of being milled or injection molded, from various metals, etc. For example, the lid and base may be made of a number of materials, including, but not limited to, copolymers, blends, laminates, polyolefins, polyesters, styrene containing polymers, polycarbonate, acrylic polymers, chlorine containing polymers, acetal homopolymers and copolymers, cellulosics and their esters, cellulose nitrate, fluorine containing polymers, polyamides, polyimides, polymethylmethacrylates, sulfur containing polymers, polyurethanes, silicon containing polymers, polyethylene, polypropylene, polystyrene, polyacrylates, silicon elastomers, TEFLON®, polyacrylate, or polycarbonate. The materials used for the device components may be rigid, flexible, or semi-flexible.

The lid (or base) is releasably mated to the base. In certain embodiments, either the base, the lid, or both, contain a releasable latch for maintaining closure, or may be close by means of an, adhesive tape, a friction closure, or a releasable clip. This list is not meant to be limiting. In certain embodiments the lid and base are connected by a hinge material which prevents the lid and base from completely separating when open.

In certain embodiments, the lid or base or both comprise "teeth," that is, raised structures which contact the flexible conduit and engage it when the lid and base are mated together, in order to increase frictional force applied to the flexible conduit and reduce slippage of the conduit through the channels.

The term "securing member" as used herein refers to any device which is used to secure the apparatus to a patient's body. By way of example, a securing member may be an adhesive pad, an adhesive strap, a hook and loop strap, a strap with snap closures, or a strap with a buckle, etc. This list is not meant to be limiting. The apparatus may be secured to any portion of a subject's body, such as the torso, a limb, the neck, a foot, a hand, etc.

The rigid base and lid are attached to the subject's body via a securing member, which in the preferred embodiment, comprises an adhesive pad, an adhesive strap, a hook and loop strap, a strap with snap closures, or a strap with a buckle.

Other embodiments of the invention will be apparent from the following detailed description, exemplary embodiments, and claims.

BRIEF DESCRIPTION OF THE DRAWINGS

FIG. 1 depicts various views of an exemplary apparatus of the present invention.

DETAILED DESCRIPTION OF THE INVENTION

Figure 1A:
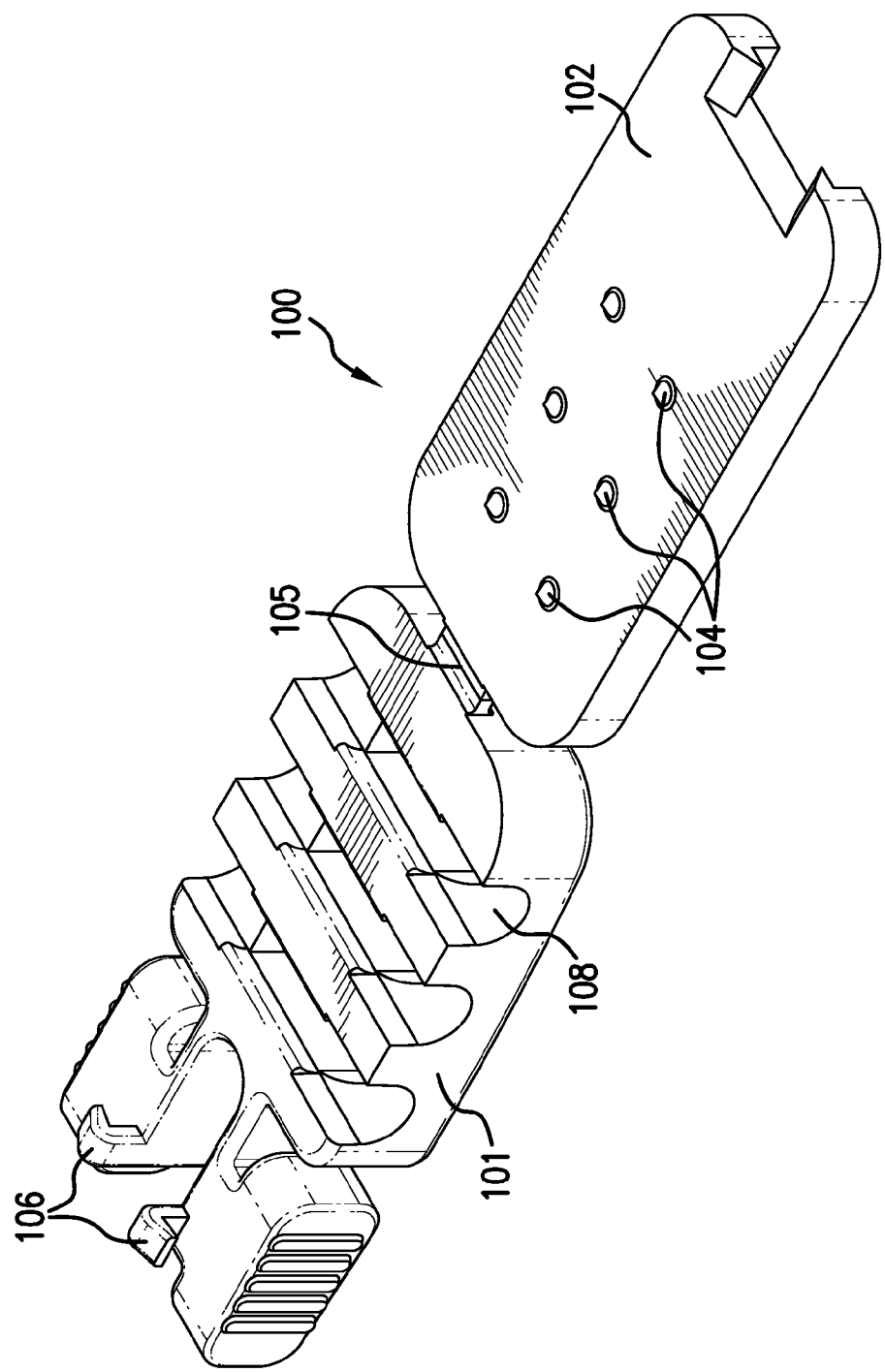
FIG. 1A depicts a top view of the exemplary apparatus in an open configuration.
Figure 1B:
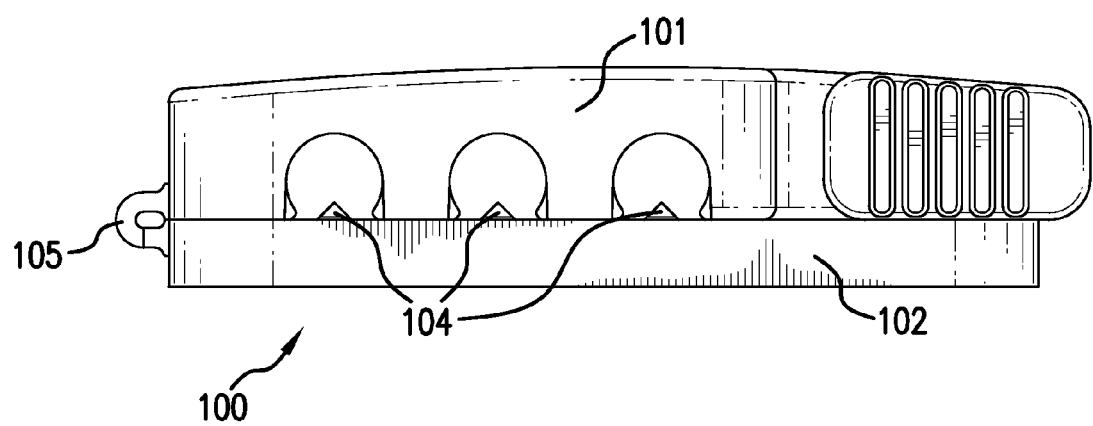
FIG. 1B depicts an edge view of the exemplary apparatus in a closed configuration, showing the engagement structures within the patent openings.
Figure 1C:
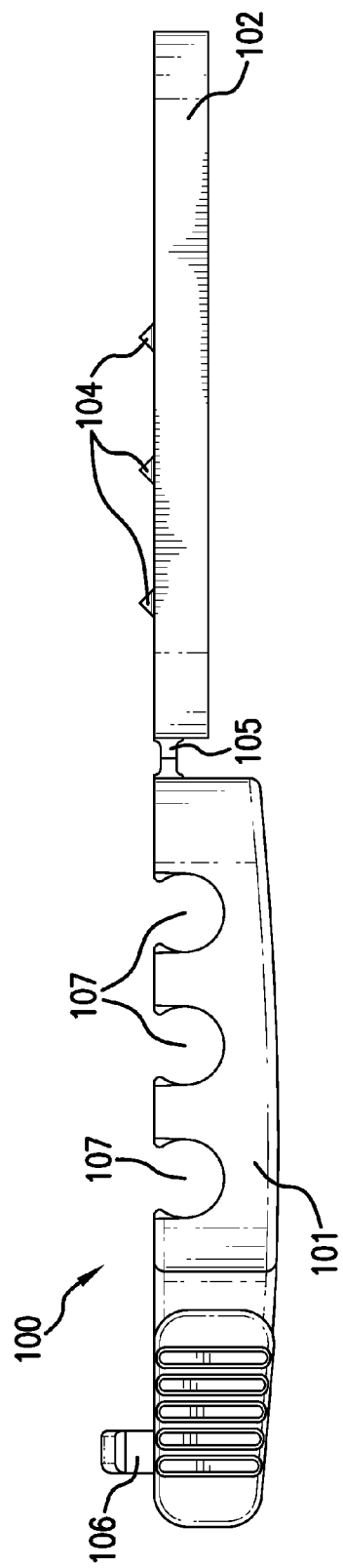
FIG. 1C depicts an edge view of the exemplary apparatus in the open configuration.
Figure 1D:
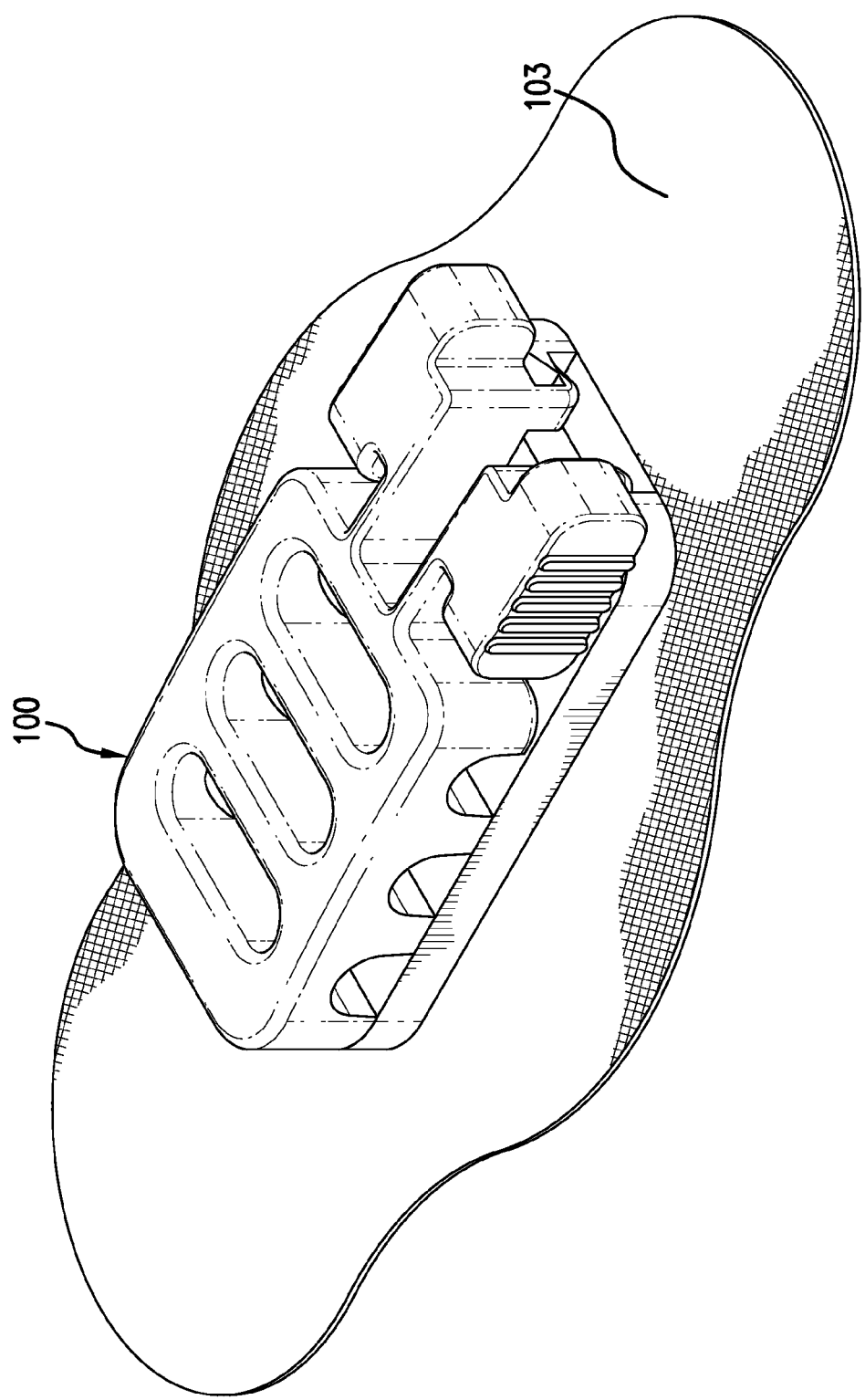
FIG. 1D depicts a top view of the exemplary apparatus comprising an adhesive patch for retaining the apparatus on a wearer.

As depicted in FIG. 1, the apparatus 100 of the present invention comprises a base 101 formed of a substantially rigid material provides three approximately parallel channels 108 that traverse the entire length of the base, and into which flexible conduit can be inserted. This base mates with a lid 102, also formed of a substantially rigid material to enclose the parallel channels. Base 101 as depicted is not solid, but includes opening in the top surface thereof. In other embodiments the lid 102 may be similarly open in configuration in order to reduce weight and material use, or both the lid and base may be made as a solid form. The rigid base 101 and lid 102 may be made out of a number of materials known in the art such as plastics, metals, and the like; for example, polypropylene, acrylates (PMMA, SMMA, etc.), styrenes (SAN, PS, ASA, ABS, etc.), polycarbonate, copolymers, ionomer resins (Surlyn), polyamides, polyesters, thermoplastic elastomers, aluminum, brass, nickel, etc.

The lid and base are held to the patient with a securing member 103. While depicted as an adhesive patch, the securing member may also be provided as a reclosable retainer, such as a flexible nylon strap which closes with a hook-and-loop closure. The lid (or base) can be attached to the securing member 103 in a number of methods known in the art, such as threading through two openings located the lid's distal ends; or by bonding of the lid to the securing member via an adhesive, heat-staking or ultra-sonic welding.

In FIG. 1, the patent portions 107 of the channels are formed entirely in the base member. In alternative embodiments, a portion of the patent portions may be provided by the lid member as well. In certain embodiments, one or more raised "tooth" structures 104 engage the conduit when it is inserted into patent portions 107 and the lid and base are mated, in order to increase frictional grip on the conduit.

A rigid lid releasably mates to the rigid base by, e.g., adhesive tape closure, a friction fit closure, or releasable clip closure, to enclose the open upper surface of each channel such that a segment of flexible conduit is retained within each channel and exits each channel at the proximal and distal opening thereof. As depicted in FIG. 1, a hinge 105 and latch 106 system provides the releasable closure of the lid and base members to one another in this embodiment. The hinge region may be a pivoting joint in which a pin on one rigid member fits into a corresponding hole on the other rigid member. Alternatively, the hinge region may simply be a flexible region which bridges the two rigid members.

Figure 2:
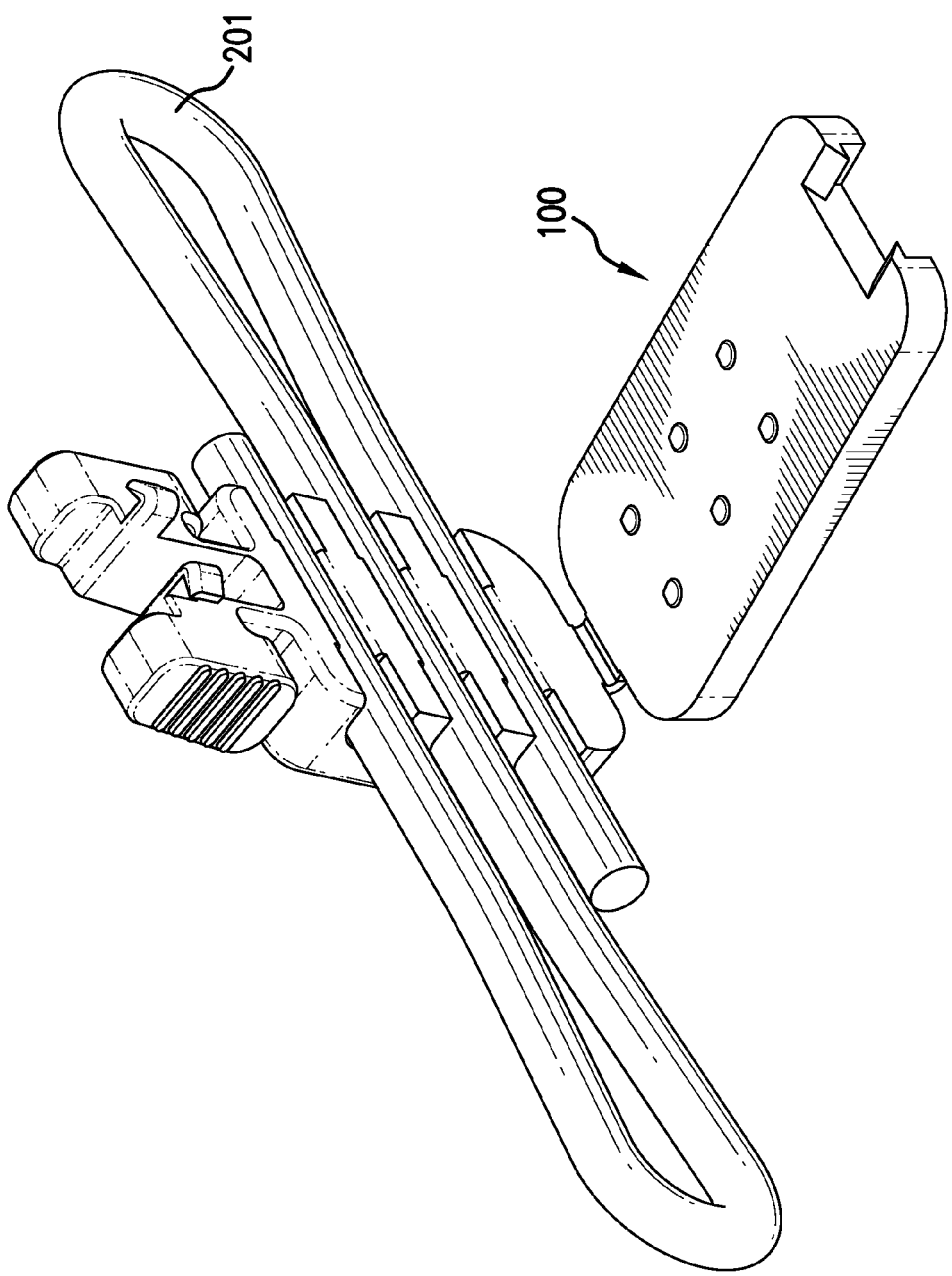
FIG. 2 depicts use of the exemplary apparatus of the invention to enclose and hold a flexible conduit.

As depicted in FIG. 2, a conduit 201 is placed into the system of channels in a proximal-to distal, distal-to-proximal, and proximal-to-distal orientation, such that the flexible conduit describes an "s" configuration between the first and second channel, and between the second and third channels. The terms "proximal" and "distal" are used for convenience of description, and are not intended to refer to an orientation relative to the subject on which the apparatus is being used.

The channels provided by the base are preferably sized such that the conduit is held by frictional forces within the channels prior to mating of the lid to the base. Mating then provides securement of the conduit until the mating of the base to the lid is reversed. Upon opening of the base and lid, the conduit may be easily removed from the channels with minimal force.

The flexible conduit can be a catheter, an intravenous tube, or an insulated cable carrying one or more conductors. The flexible conduit is adjusted by the method of moving of the loop of each portion of this "s" configuration to conform to size of the subject or the distance on the subject which needs to be traversed by the conduit.

Figure 3:
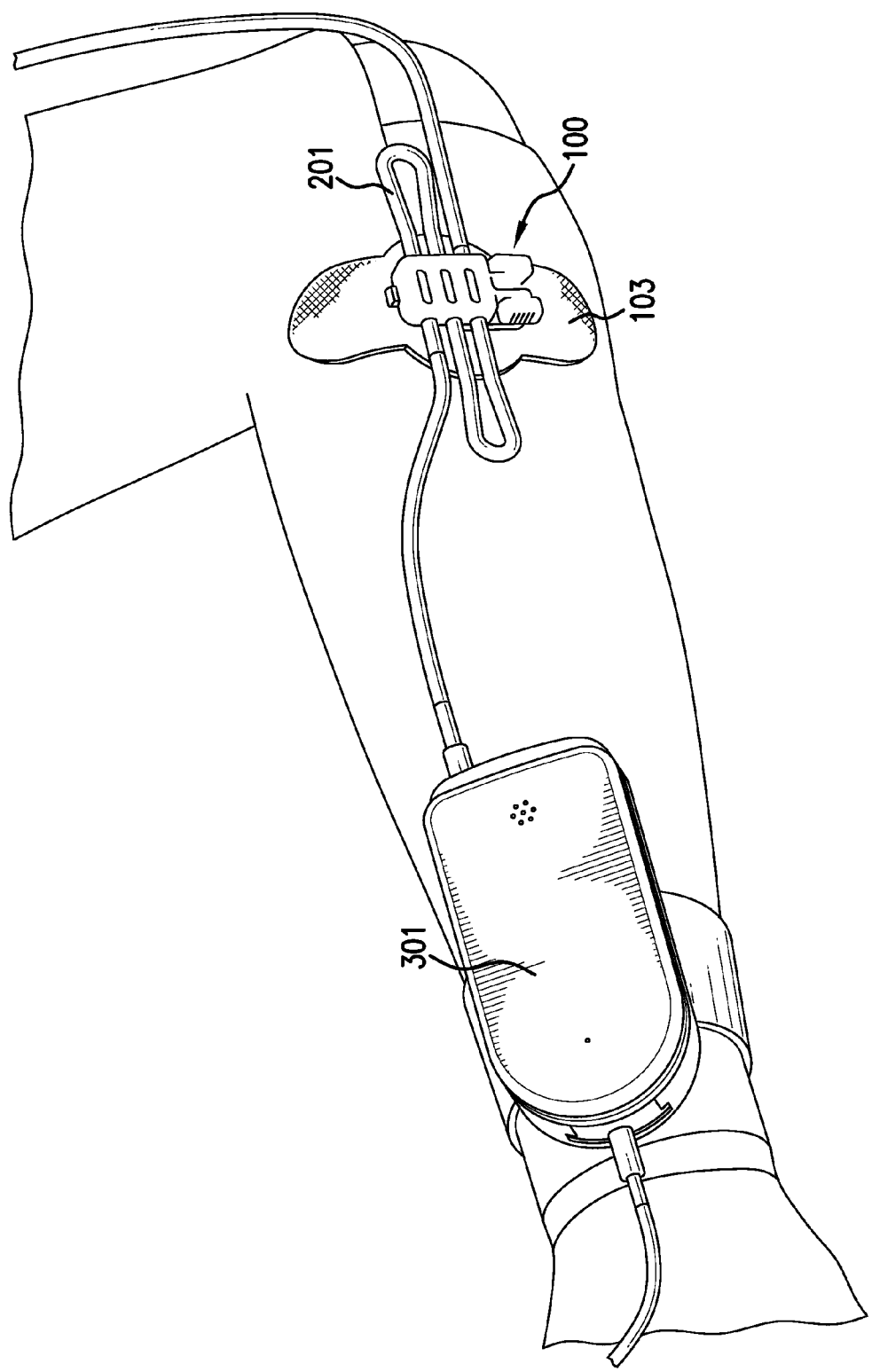
FIG. 3 depicts attachment of the exemplary apparatus of the invention for conduit management on a patient's limb.

FIG. 3 depicts the apparatus 100 deployed on the arm of a subject. In this figure, an adhesive securing member is placed on the arm in a desired location. Removal of the apparatus is performed by simply removing the adhesive patch 103. The apparatus is preferably designed as a disposable component. As used herein, the term "disposable" refers to the characteristic that the lid, base, and associated securing member may be disengaged as a single component from conduit 201 in the course of normal use by the user such that the conduit may be easily separated from, and need not be discarded with, the apparatus. In FIG. 3, conduit 201 is depicted as a cable providing electrical communication to other electronic modules 301.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. An apparatus adapted to secure a flexible conduit to a subject's body and to adjust the length of the flexible conduit to conform to the portion of the subject's body being traversed by the flexible conduit, comprising:

a rigid base comprising three approximately parallel elongate channels, each channel having a proximal opening at a first end of the base and a distal opening at a second end of the base, and each channel having an open upper surface into which the flexible conduit is inserted to traverse the length of the channel;

a rigid lid which releasably mates to said base to enclose the open upper surface of each elongate channel such that a segment of the flexible conduit is retained within each channel and exits each channel at the proximal and distal opening thereof, the flexible conduit describing an "S" configuration by traversing a first of said three channels in a proximal-to-distal orientation, traversing a second of said three channels in a distal-to-proximal orientation, and traversing a third of said three channels in a proximal-to-distal orientation, wherein adjusting the length of each loop of the "S" configuration adjusts the length of the flexible conduit to conform to the portion of the subject's body being traversed by the flexible conduit, and wherein portions of the lid which contact the segment of the flexible conduit retained within each channel comprise one or more raised structures which, upon mating of the base and lid, engage without encircling the segment of the flexible conduit to reduce slippage of the flexible conduit through the channel by increasing frictional force applied to the flexible conduit; and a securing member configured to releasably secure the mated base and lid on the body of the subject.

2. The apparatus of claim 1, wherein the base and lid are secured to one another by a hinge region.

3. The apparatus of claim 2, wherein the base and lid are mated to one another by an adhesive tape closure.

4. The apparatus of claim 2, wherein the base and lid are mated to one another by a friction fit closure.

5. The apparatus of claim 2, wherein the base and lid are mated to one another by a releasable clip closure.

6. The apparatus of claim 1, wherein the flexible conduit comprises a catheter.

7. The apparatus of claim 1, wherein the flexible conduit comprises an intravenous tube.

8. The apparatus of claim 1, wherein the flexible conduit comprises an insulated cable carrying one or more conductors.

9. The apparatus of claim 1, wherein the securing member comprises an adhesive pad, an adhesive strap, a hook and loop strap, a strap with snap closures, or a strap with a buckle.

10. A method of securing a flexible conduit to a subject's body and adjusting the length of said flexible conduit to conform to the portion of the subject's body being traversed by the flexible conduit, comprising:

affixing the apparatus of claim 1 to the body of the subject using a securing member configured to releasably secure the base and lid on the body of the subject;

inserting the flexible conduit into each of the three approximately parallel elongate channels of the apparatus, such that a segment of the flexible conduit is retained within each channel and exits each channel at the proximal and distal opening thereof, the flexible conduit describing an "S" configuration by traversing the first of said three channels in a proximal-to-distal orientation, traversing the second of said three channels in a distal-to-proximal orientation, and traversing the third of said three channels in a proximal-to-distal orientation;

adjusting the length of each loop of the "S" configuration to adjust the length of the flexible conduit to conform to the portion of the subject's body being traversed by the flexible conduit; and releasably mating the lid and base of the apparatus.

11. The method of claim 10, wherein the base and lid are secured to one another by a hinge region.

12. The method of claim 11, wherein the base and lid are mated to one another by an adhesive tape closure.

13. The method of claim 11, wherein the base and lid are mated to one another by a friction fit closure.

14. The method of claim 11, wherein the base and lid are mated to one another by a releasable clip closure.

15. The method of claim 10, wherein the flexible conduit comprises a catheter.

16. The method of claim 10, wherein the flexible conduit comprises an intravenous tube.

17. The method of claim 10, wherein the flexible conduit comprises an insulated cable carrying one or more conductors.

18. The method of claim 10, wherein the securing member comprises an adhesive pad, an adhesive strap, a hook and loop strap, a strap with snap closures, or a strap with a buckle.

19. The method of claim 10, wherein the attachment point on a subject's body comprises a limb, and wherein the flexible conduit is longer than the subject's limb and is adjusted such that the length traversed by the flexible conduit is less than the length of the subject's limb.

20. The method of claim 19, wherein the limb is an arm.

* * * * *